United States Patent [19]

Dannels et al.

[11] Patent Number: 4,873,382

[45] Date of Patent: Oct. 10, 1989

[54] PURIFICATION OF TELOMERS PREPARED FROM CHLOROTRIFLUOROETHYLENE AND TRICHLOROTRIFLUOROETHANE

[75] Inventors: Bobby F. Dannels; Deborah J. Olsen, both of Grand Island; John Forcucci, Niagara Falls, all of N.Y.

[73] Assignee: Occidential Chemical Corporation, Niagara Falls, N.Y.

[21] Appl. No.: 234,645

[22] Filed: Aug. 22, 1988

Related U.S. Application Data

[63] Continuation-in-part of Ser. No. 116,843, Nov. 5, 1987.

[51] Int. Cl.[4] .................... C07C 17/24; C07C 17/38; C07C 19/08
[52] U.S. Cl. ...................................... 570/177; 570/172
[58] Field of Search ......................................... 570/177

[56] References Cited

U.S. PATENT DOCUMENTS

| | | | |
|---|---|---|---|
| 3,388,175 | 6/1968 | Viney | 570/177 |
| 4,102,981 | 7/1978 | Woychesin et al. | 570/177 |
| 4,129,603 | 12/1978 | Bell | 570/177 |
| 4,766,261 | 8/1988 | Bierl | 570/177 |

FOREIGN PATENT DOCUMENTS 233839 3/1986 German Democratic Rep. ..................................... 570/177

Primary Examiner—J. E. Evans
Attorney, Agent, or Firm—James F. Tao; William G. Gosz; Arthur S. Cookfair

[57] ABSTRACT

A mixture of telomers prepared by reacting chlorotrifluoroethylene with 1,1,2-trichlorotrifluoroethane ($CCl_2FCF_2Cl$) is purified by reacting the telomer mixture with potassium hydroxide in the presence of a quarternery ammonium compound and, optionally, a glycol, separating and removing impurities from the telomer mixture, subsequently reacting the telomer with potassium permanganate in the presence of the quarternery ammonium compound in a solvent, and recovering a purified telomer mixture.

If additional purity is required, the purified telomer mixture can be heated to a temperature of from about 150° C. to about 250° C. for at least 12 hours, and impurities formed during the thermal treatment are removed.

The purified telomers of this invention find uses in applications requiring the use of non-flammable hydraulic fluids.

11 Claims, No Drawings

PURIFICATION OF TELOMERS PREPARED FROM CHLOROTRIFLUOROETHYLENE AND TRICHLOROTRIFLUOROETHANE

CROSS-REFERENCE TO RELATED APPLICATION

This application is a continuation-in-part of U.S. application Ser. No. 116,843, filed Nov. 5, 1987.

BACKGROUND OF THE INVENTION

The present invention relates to a process for purifying telomers of the formula $CF_2ClCFCl(CF_2CFCl)_nCl$, where n is in the range of 1 to 10. The telomers of this invention are saturated, low molecular weight polymers which are useful for preparing non-flammable hydraulic fluids.

Various methods of preparing chlorotrifluoroethylene ("CTFE") telomers are known in the prior art and have been practiced commercially for many years. An article by William T. Miller, Jr. et al in *Industrial and Engineering Chemistry*, pages 333–337 (1947), entitled "Low Polymers of Chlorotrifluoroethylene", describes a process for producing low molecular weight polymers of CTFE by polymerization in a solution of chloroform using benzoyl peroxide as a polymerization promoter. Other solvents disclosed in the reference as being useful for this purpose include carbon tetrachloride and tetrachloroethylene. The solution is heated in a pressure vessel for 1¾ hours at 100° C., and the unreacted CTFE monomer and chloroform are removed by distillation, leaving a crude telomer of general formula $CHCl_2(CF_2CClF)_nCl$, which can be further heated and distilled to yield products ranging from a light oil to a semi-solid wax or grease.

Another process for preparing low molecular weight CTFE polymers is described in U.S. Pat. No. 2,788,375, issued Apr. 9, 1957. This process comprises reacting CTFE with a saturated brominated compound in the presence of a source of radiation. Suitable brominated compounds include 1,2-dibromo-2-chlorotrifluoroethane ($CF_2BrCClFBr$). The saturated bromopolychlorofluoro compounds obtained by this process can then be distilled, and the isolated fractions reacted with chlorine to prepare polychlorofluoro compounds. The compounds are predominantly higher molecular weight telomers, i.e. n is greater than 4.

A more recent development in this field is described in a series of articles by Y. Pietrasanta et al entitled "Telomerization by Redox Catalysis" appearing in the *European Polymer Journal*, Vol. 12 (1976). This technology involves the reaction of single carbon halogenated telogens, such as $CCl_4$ and $CCl_3Br$, with CTFE in the presence of benzoin and a suitable redox catalyst, such as ferric chloride. The telomerization reaction is suitably carried out in acetonitrile which is a common solvent for the reactants and catalysts. The telomerization reaction can be illustrated as follows:

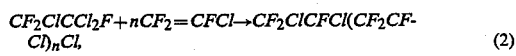

$$CCl_3 + nCF_2=CFCl \xrightarrow{FeCl_3}{Benzoin} CCl_3(CF_2CFCl)_nX \quad (1)$$

where X is chlorine or bromine. The reference further discloses that the use of $CCl_3Br$ as a telogen results in a lower degree of telomerization and a higher proportion of monoaddition product than would occur with the use of $CCl_4$.

The redox process has the advantage of directly preparing low molecular weight products without the necessity of cracking or fractionating a higher molecular weight polymer.

A modification of the redox process is disclosed in commonly assigned U.S. application Ser. No. 116,843, filed Nov. 5, 1987. This modification involves the telomerization reaction of chlorotrifluoroethylene with 1,1,2-trichlorotrifluoroethane in a nitrile group-containing solvent, such as acetonitrile, propionitrile and ethyl cyanoacetate, in the presence of a catalytic amount of metallic iron or stainless steel type 410-L, which is an alloy of 87.5% iron and 12.5% chromium. Optionally a halide-containing compound selected from the group consisting of LiCl, $FeCl_3$, $MoCl_5$, tetramethyl ammonium chloride, tetrabutyl ammonium bromide, triethylamine hydrochloride and n-chlorosuccinide, can also be added to the reaction mixture. The halide-containing compound functions as a chain-terminating agent during the reaction to limit the formation of higher molecular weight species. This process can be illustrated as follows:

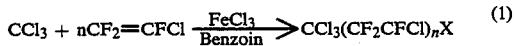

$$CF_2ClCCl_2F + nCF_2=CFCl \rightarrow CF_2ClCFCl(CF_2CFCl)_nCl \quad (2)$$

where n is in the range of 1 to 10.

Reaction (2) results in the preparation of a mixture or distribution of individual telomer species having molecular weights corresponding to n values of from 1 to 10, rather than pure isomers having a discrete structure, i.e. a single n value. Separation of the individual telomer species from the mixture is accomplished by distillation using procedures well known to those skilled in this art.

Although telomers produced according to this latter process represent a significant advance over the prior art, such telomers have been found to contain minor amounts of impurities which can present corrosion problems when used in demanding applications such as nonflammable hydraulic fluids. An efficient and economically feasible purification process for such telomers would therefore be highly desirable.

SUMMARY OF THE INVENTION

In accordance with the present invention, a process for purifying a telomer mixture prepared by reacting chlorotrifluoroethylene with 1,1,2-trichlorotrifluoroethane comprises the steps of (A) reacting the telomer mixture with an aqueous solution of sodium or potassium hydroxide in the presence of a quarternary ammonium compound and, optionally, a glycol, (B) separating and removing impurities from the telomer mixture of step A, (C) reacting the telomer mixture from step B with sodium or potassium permanganate in a solvent in the presence of a quarternary ammonium compound, and (D) recovering a purified telomer mixture.

The purified telomer mixture can be further purified by heating the mixture to a temperature from about 150° C. to about 250° C. for at least about 12 hours, removing impurities formed during the thermal treatment, and reacting the telomer mixture with potassium permanganate in a solvent.

The preferred quarternary ammonium compound is tricaprylylmethylammonium chloride, the preferred glycols are diethylene glycol and polyethylene glycol, and the preferred solvent is acetonitrile.

DESCRIPTION OF THE PREFERRED EMBODIMENTS

The telomer mixture which is purified according to the process of the present invention is prepared by reacting chlorotrifluoroethylene with 1,1,2-trichlorotrifluoroethane ($CCl_2FCF_2Cl$) in the presence of metallic iron or stainless steel type 410-L, and optionally a halide-containing compound, to produce telomers having the structural formula $CF_2ClCFCl(CF_2CFCl)_nCl$, where n is in the range of 1 to 10. This process is more fully described in co-pending U.S. application Ser. No. 116,843, filed Nov. 5, 1987, the disclosure of which is incorporated by reference herein.

In addition to the desired distribution of telomers produced by the reaction of chlorotrifluoroethylene and 1,1,2-trichlorotrifluoroethane, minor amounts of impurities are also co-produced in this reaction. These impurities tend to be reactive components in the fluid. Since the utility of the telomers is generally based upon their inertness to both chemical and thermal attack, the reactivity of the impurities is detrimental in the end use of the telomers. Consequently, it is desirable to either remove the impurities from the telomers or to render the impurities substantially inert. The present invention accomplishes both of these objectives.

The impurities which are removed according to the process of this invention include species which contain hydrogen, species which have an unstable arrangement of halogens, species which contain nitrogen, as well as olefinic or unsaturated impurities which tend to be the most reactive.

The first step of the purification process involves reacting the telomer mixture (or individual telomer species which contain these impurities) with an aqueous solution of potassium hydroxide in the presence of a catalytic amount of a quarternary ammonium compound and, optionally, a glycol at a temperature of from about 50° C. to about 150° C. for about at least 24 hours. Both the quarternary ammonium compound and, optionally, the glycol function as co-catalysts in this reaction. The quarternary ammonium compound is preferably tricaprylylmethylammonium chloride, and the preferred glycols are diethylene glycol and polyethylene glycol. Amounts of quarternary ammonium compound of from about 0.05% to about 0.5%, and amounts of glycol component of from about 5% to about 20%, all by weight of the telomer mixture, are operable in this invention, although lesser and greater amounts of these catalysts can also be used.

This reaction results in the conversion of most of the impurities, such as hydrogen-containing species, species which have an unstable arrangement of halogen, or olefinic species, into a soft tar-like solid that forms at the interphase between the product and the aqueous phase, and this solid can be easily removed by methods such as decantation, etc. The use of drastic reaction conditions, such as elevated temperatures, etc., have not been found to have any beneficial effect on this reaction, and can actually increase the loss of useful product. For instance, drastic reaction conditions tend to increase the amount of tar formed during the reaction, making it more difficult to remove and separate from the product.

Basic impurities in the telomers can be steam distilled off, if desired, during the reaction of the telomer mixture with potassium hydroxide for even higher purity.

After reacting the telomer mixture with potassium hydroxide as indicated above, the recovered telomer mixture is then reacted with potassium permanganate at room temperature. This reaction is also carried out in the presence of a catalytic amount, preferably from about 0.5% to about 2% by weight of telomer mixture, of a quarternary ammonium compound. The preferred quarternary ammonium compound is once again tricaprylylmethylammonium chloride. The presence of a glycol component is not required in this reaction, although a solvent is necessary and preferably that solvent is acetonitrile. This reaction is carried out until the potassium permanganate maintains its reddish color for about 8 hours. Typical reaction times are from about 24 to 48 hours.

After the potassium permanganate reaction is completed, solid manganese dioxide particles are filtered from the reaction mixture, and the lower product layer is separated and recovered. The recovered and purified telomer mixture can be subsequently treated with alumina, preferably activated alumina, or Maglite D, a light magnesium oxide product sold by Merck & Co., Inc., if desired, to further improve its corrosion resistant properties when used as a non-flammable hydraulic fluid.

The potassium permanganate reaction is carried out at about room temperature since this is the most convenient temperature and since the use of higher temperatures does not produce any apparent advantage. The replacement of acetonitrile with water results in the precipitation of a very fine suspension of manganese dioxide that is difficult to filter, and therefore the use of water should be avoided.

Treatment with potassium permanganate is effective to remove residual unsaturated species which are not removed by treating the telomer mixture with potassium hydroxide.

The purified telomer which is recovered after treatment with potassium permanganate can be further purified, if desired, by heating the telomer mixture to an elevated temperature of from about 150° C. to about 250° C. for at least about 12 hours. This procedure has the effect of removing thermally unstable species which may be still present in the telomer. These species form solids which can be conveniently removed from the telomer mixture by filtration.

After the desired degree of purity has been achieved, the telomer mixture can be distilled using a suitable distillation column. A particulary desirable telomer is one having 6 carbon atoms, and this telomer can be obtained in relatively high purity using this process.

The following example is intended to further illustrate the various embodiments and advantages of the present invention without limiting it thereby. This example illustrates the purification of telomers according to the process of the present invention.

EXAMPLE

A crude telomer mixture is obtained by reacting chlorotrifluoroethylene with 1,1,2-trichlorotrifluoroethane in accordance with the procedure described in U.S. patent application Ser. No. 116,843, filed Nov. 5, 1987. This crude telomer mixture was evaluated for the presence of oxidizable material using the potassium permanganate test. According to this test, approximately 1 gram of sample is added to a test tube and dissolved with 10 ml. of acetone. 0.06 ml. of a 1% potassium permanganate solution is added to the sample, and the time after the addition of the potassium permanganate to the end-point is noted. The end-point is when the color remaining is equal to a color standard, which is basically colorless. The entire test is run at about 25° C. The crude telomer, when tested as described, had a $KM_nO_4$ time interval of only a few minutes.

The crude telomer is then reacted with an equal volume of 25% aqueous potassium hydroxide using tricaprylylmethylammonium chloride and diethylene glycol as co-catalysts at 110° C. to 120° C. for 24 hours. The reaction is conducted in a Morton-type flask to insure the necessary mixing of the two-phase reaction mixture.

Approximately 3% of the telomer mixture is converted into a soft tar-like solid that is removed from the interphase between the product and the aqueous phase. The amount of product recovered is in the range of 90% to 95%.

The purified product from the potassium hydroxide reaction is recovered and reacted with potassium permanganate at room temperature. This reaction is conducted using an equal volume of acetonitrile and tricaprylylmethylammonium chloride as a catalyst. The reaction time is from 1 to 2 days, and the potassium permanganate is added incrementally until its red color persists for about 8 hours. This indicates that the reaction is substantially completed.

Upon completion of the reaction, the solid manganese dioxide is filtered off, and the lower product layer is separated. Approximately two-thirds of the telomer charged remains after treatment with potassium permanganate. The overall product recovered can be increased to about 84% to 90% by recovering additional product from the manganese dioxide solids and the acetonitrile. The manganese dioxide solids can be suspended in water and reacted with sulfur dioxide to convert the manganese dioxide to soluble manganese sulfate. The telomers contained in the manganese dioxide solids, approximately 10% of the total, can then be separated as the lower layer. Similarly, the acetonitrile layer can be diluted with water to recover an additional 10% of the total telomer product. When tested as described above, the purified telomer had a $KMnO_4$ time internal of greater than 8 hours.

While various embodiments and exemplifications of this invention have been shown and described in this specification, modifications and variations thereof will be readily appreciated by one skilled in the art. It is to be understood, therefore, that the appended claims are intended to cover all such modifications and variations which are considered to be within the scope and spirit of the present invention.

What is claimed is:

1. A process for purifying a mixture of telomers prepared by reacting chlorotrifluoroethylene with $CF_2ClCFCl_2$, said telomers having the formula $CF_2ClCFCl(CF_2CFCl)_nCl$, where n is in the range of 1 to 10, said process comprising the steps of
   (a) reacting the telomer mixture with an aqueous solution of potassium hydroxide in the presence of a quarternary ammonium compound,
   (b) separating and removing impurities from the telomer mixture of step (a),
   (c) reacting the telomer mixture from step (b) with potassium permanganate in a solvent in the presence of a quarternary ammonium compound, and
   (d) recovering a purified telomer mixture.

2. The process of claim 1 wherein the quarternary ammonium compound is tricaprylylmethylammonium chloride.

3. The process of claim 1 wherein glycol is also present during the reaction step (a).

4. The process of claim 3 wherein the glycol is diethylene glycol.

5. The process of claim 3 wherein the glycol is polyethylene glycol.

6. The process of claim 1 wherein the reaction in step (a) is conducted at a temperature in the range of from about 50° C. to about 150° C.

7. The process of claim 1 wherein the quarternary ammonium compound is present in the reaction mixture of step (a) in an amount of from about 0.05% to about 0.5% by weight of the telomer mixture.

8. The process of claim 1 wherein the quarternary ammonium compound is present in the reaction mixture of step (c) in an amount of from about 0.5% to about 2% by weight of the telomer mixture.

9. The process of claim 3 wherein the glycol is present in the reaction mixture of step (a) in an amount of from about 5% to about 20% by weight of the telomer mixture.

10. The process of claim 1 wherein the solvent is acetonitrile.

11. The process of claim 1 wherein the telomer mixture of step (d) is heated to a temperature of from about 150° C. to about 250° C. for at least 12 hours, and additional impurities are removed from the telomer mixture.

* * * * *